United States Patent
Adams et al.

(10) Patent No.: US 10,323,931 B2
(45) Date of Patent: Jun. 18, 2019

(54) METHOD AND SYSTEM FOR ALIGNING A TERAHERTZ SENSOR SYSTEM

(71) Applicant: Ford Motor Company, Dearborn, MI (US)

(72) Inventors: Scott Adams, Milan, MI (US); Marina Baker, Southgate, MI (US); Mark Nichols, Saline, MI (US); Tony Misovski, Oxford, MI (US)

(73) Assignee: Ford Motor Company, Dearborn, MI (US)

( * ) Notice: Subject to any disclaimer, the term of this patent is extended or adjusted under 35 U.S.C. 154(b) by 0 days.

(21) Appl. No.: 15/795,479

(22) Filed: Oct. 27, 2017

(65) Prior Publication Data
US 2019/0128661 A1    May 2, 2019

(51) Int. Cl.
*G01B 11/06* (2006.01)
*G01N 21/55* (2014.01)
(Continued)

(52) U.S. Cl.
CPC ........ *G01B 11/0633* (2013.01); *B05B 12/084* (2013.01); *B25J 9/1679* (2013.01); *G01B 11/0683* (2013.01); *G01N 21/55* (2013.01); *G01N 33/32* (2013.01); *B29C 2948/92152* (2019.02)

(58) Field of Classification Search
CPC ....... G01B 11/02; G01B 11/06; G01B 11/026; G01B 11/245; G01B 11/0633; G01B 11/0691; G01B 11/0683; B05B 12/084; B25J 9/16; B25J 9/1679; G01N 21/55; G01N 21/3581; G01N 33/32; B29C 2947/92152; B05C 11/10; B05D 7/00
See application file for complete search history.

(56) References Cited

U.S. PATENT DOCUMENTS

2010/0195092 A1    8/2010 Ohtake
2015/0212060 A1    7/2015 Van Mechelen et al.
(Continued)

FOREIGN PATENT DOCUMENTS

| WO | 2017/012699 | 1/2017 | |
|----|---|---|---|
| WO | 2017/101906 | 6/2017 | |
| WO | WO 2017101906 A1 * | 6/2017 | ........... G01B 11/026 |

OTHER PUBLICATIONS

Su, K. et al., Terahertz Sensor for Non-Contact Thickness and Quality Measurement of Automobile Paints of Varying Complexity, IEEE Transactions on Terahertz Science and Technology, vol. 4(4), pp. 432-439, Jul. 2014, available at URL http://ieeexplore.ieee.org/document/6827225/.

*Primary Examiner* — Jamil Ahmed
(74) *Attorney, Agent, or Firm* — Burris Law, PLLC

(57) ABSTRACT

The present disclosure is directed toward a method for aligning a radiation head of a terahertz sensor system with a target surface. The method includes: scanning a selected area of the target surface with a terahertz radiation beam emitted by the radiation head; sensing a peak amplitude for each reflected radiation signal from a plurality of reflected radiation signals received by the radiation head during the scanning of the selected area; and identifying a normal position of the radiation head with respect to the target surface based on a maximum peak amplitude from among the peak amplitudes of the reflected radiation signals.

20 Claims, 6 Drawing Sheets

(51) Int. Cl.
    *G01N 33/32*     (2006.01)
    *B05B 12/08*     (2006.01)
    *B25J 9/16*     (2006.01)

(56) References Cited

U.S. PATENT DOCUMENTS

2017/0023354 A1    1/2017   Stitch
2017/0050208 A1*   2/2017   Nichols .................. B25J 9/1679

\* cited by examiner

METHOD AND SYSTEM FOR ALIGNING A TERAHERTZ SENSOR SYSTEM

FIELD

The present invention relates to a system and method for aligning a terahertz radiation beam with a surface to measure a thickness of multiple paint layers on the surface.

BACKGROUND

The statements in this section merely provide background information related to the present disclosure and may not constitute prior art.

The exterior of a vehicle generally includes multiple layers of paint and/or other coatings, such as electrocoat, primer, basecoat, and clear coat. Each layer has a minimum film build designed to inhibit the degradation and potential delamination of the exterior due to for example, UV, and visible light, and to provide corrosion protection, and enhance the vehicle's appearance.

While various paint thickness measurement techniques are available for measuring a single layer of paint, there are a limited number of non-destructive measurement techniques for measuring multiple layers. One such measurement technique utilizes ultrasound technology in which an ultrasonic transducer is placed on the exterior surface, and sends an ultrasonic signal through the exterior surface. A liquid couplant, usually water, is used to transmit the signal into the coating material. The ultrasonic signal generates an echo at the layer interfaces, and the thickness is determined based on the time difference between the successive echoes. Sound velocity values vary among the different coatings, so calibration is performed on all layers in addition to the various basecoat colors.

While the ultrasound technique is effective, there are some issues with this technique. For example, the transducer size and the tool used with the transducer may not allow measurement of certain vehicle surfaces, such as a windshield flange, and thus, a separate procedure is usually employed to obtain data of those areas. Another issue is that the transducer requires a large (e.g., 10 mm diameter) flat area in order to generate adequate waveforms. This requires selecting points on a vehicle based on their flatness rather than being able to select locations on the vehicle that are of interest but may not be flat. Furthermore, the transducer physically contacts the vehicle. Although damage from the transducer may not occur, the water left on the body of the vehicle affects other quality control processes, such as a dirt detection quality check.

Another technique for measuring a multi-layer surface includes the use of a radiation beam having a terahertz (THz) frequency. Using a THz light source to generate a THz radiation beam, a THz radiation head is positioned at a designated offset and is normal to a target surface of the vehicle before the measurement is performed. For example, the radiation head can be attached to a robot or some other piece of automation to allow it to contour surfaces and complex geometries. The THz radiation beam is emitted from the Thz radiation head and reflects off the vehicle due to a change in refractive index. The time difference between the emission and reflection is used to calculate the thickness.

Since the THz head is fairly compact and does not contact the surface of the vehicle, it can be used to measure places not measurable by an ultrasonic transducer, such as the windshield flange. The THz radiation beam is typically 1 mm in diameter which enables measurement of multiple regions that have a flat section of that size.

However, for an optimal measurement, the THz radiation head should be aligned normal to a target surface of the vehicle so that the emitter of the radiation head aligns with the detector of the radiation head. When the emitter and detector are aligned, the amplitude of the reflected radiation signal from the detector is usually at the maximum value. If the radiation head is not normal to the surface, the reflected radiation signal may not align with the detector, which results in a lower peak amplitude. This loss in signal may affect the results of the thickness measurement. Misalignment during the calibration procedure would also result in an incorrect calibration file and bad data. These and other issues are addressed by the teachings of the present disclosure.

SUMMARY

This section provides a general summary of the disclosure, and is not a comprehensive disclosure of its full scope or all of its features.

In one form, the present disclosure is directed to a method for aligning a radiation head of a terahertz sensor system with a target surface. The method includes: scanning a selected area of the target surface with a terahertz radiation beam emitted by the radiation head; sensing a peak amplitude for each reflected radiation signal from a plurality of reflected radiation signals received by the radiation head during the scanning of the selected area; and identifying a normal position of the radiation head with respect to the target surface based on a maximum peak amplitude from among the peak amplitudes of the reflected radiation signals.

In another form, the method further includes determining an estimated normal of the radiation head with respect to the target surface, where the selected area surrounds the estimated normal.

In yet another form, the scanning of the selected area further includes scanning a plurality of points in the selected area with the estimated normal being one of the plurality of points.

In one form, the plurality of points is distributed in the selected area at a selected step size forming a two-dimensional region around the estimated normal.

In another form, the determining the estimated normal further includes: emitting, by a light source, a visible light beam toward the target surface to generate one or more illuminated points on the target surface; and identifying a position of the radiation head relative to the target surface as the estimated normal when one illuminated point is visible on the target surface.

In yet another form, the method further includes generating a displacement control map of the selected area. The displacement control map associates the peak amplitudes of the reflected radiations signals with regions of the selected area from which the reflected radiation signal originated from.

In one form, the region associated with the maximum peak amplitude from among the peak amplitudes is indicative of the normal position of the radiation head with respect to the selected area.

In another form, the scanning of the selected area further includes: adjusting, by way of a moveable member, an angular position of the radiation head with respect to the target surface to scan a plurality of points that are distributed in the selected area; and at each of the plurality of points, emitting the terahertz radiation beam and receiving at least one of the reflected radiation signals from the plurality of reflected radiation signals.

In one form, the method further includes generating a displacement control map that associates the plurality of points with respective peak amplitudes.

In one form, the present disclosure is directed toward a terahertz sensor system that includes a moveable member and a terahertz sensor. The terahertz sensor includes a radiation head attached to the moveable member. The radiation head is operable to emit a radiation beam and receive one or more reflected radiation beams reflected from a target surface. The terahertz sensor includes a controller configured to analyze a peak amplitude of a reflected radiation signal that is indicative of the reflected radiation beam. The controller is configured to operate the moveable member to scan a selected area of the target surface with the radiation beam, and identify a normal of the radiation head with respect to the target surface based on a maximum peak amplitude from among a plurality of peak amplitudes for a plurality of reflected radiation signals obtained during the scan.

In another form, the controller is configured to identify an estimated normal of the radiation head with respect to the target surface, and define the selected area such that the estimated normal is within the selected area.

In yet another form, the controller is configured to scan a plurality of points in the selected area with the estimated normal being one of the plurality of points.

In one form, the system further includes a visible alignment tool that includes a light source arranged with the radiation head. The controller is configured to operate the light source to emit a visible light toward the target surface, and to identify an estimated normal of the radiation head relative to the target surface when the visible alignment tool generates one visible point along the target surface.

In another form, the controller is configured to adjust an angular position of the radiation head with respect to the target surface by way of the moveable member to scan a plurality of points that are distributed in the selected area, and at each of the plurality of points, the controller operates the radiation head to emit the terahertz radiation beam and receive the reflected radiation beam.

In yet another form, with the radiation head located normal with the target surface, the controller is configured to operate the radiation head to emit the radiation beam and to determine the thickness of one or more coatings on the target surface based on the reflected radiation beam.

In one form, the moveable member is a robotic arm for adjusting the position of the radiation head.

In one form, the present disclosure is directed toward a method for aligning a terahertz radiation head. The method includes: scanning a selected area of the target surface with a terahertz radiation beam via the radiation head; sensing a peak amplitude for each of a plurality of reflected radiation signals during the scanning of the selected area; and identifying a normal of the radiation head relative to the target surface based on a maximum peak amplitude from among the peak amplitudes.

In another form, the scanning of the selected area further includes: adjusting, by way of a moveable member, an angular position of the radiation head to scan a plurality of points that are distributed in the selected area; and at each of the plurality of points, emitting the radiation beam and detecting at least one of the reflected radiation signals from the plurality of reflected radiation signals.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1A:
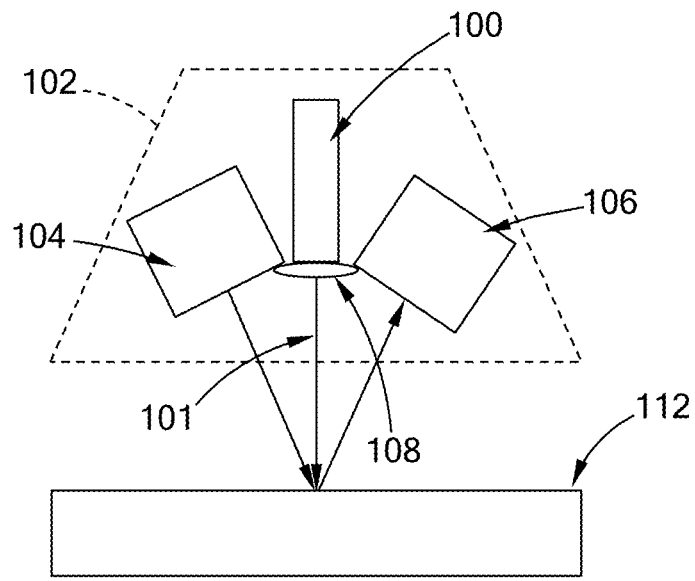
FIGS. 1A and 1B illustrate a visual alignment tool that includes a laser device for aligning a radiation head of a terahertz sensory system.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1B:
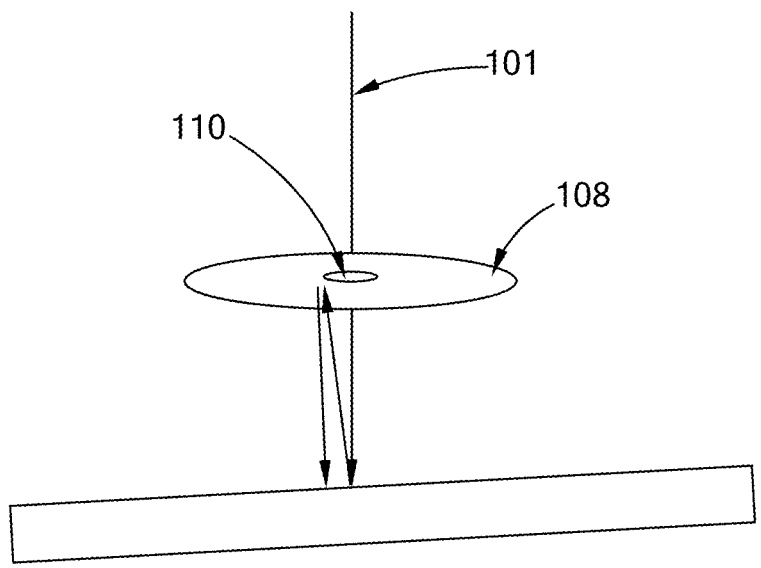

A terahertz radiation beam is not visible to the human eye, and thus it may be difficult to align a radiation head, such that is its perpendicular to a target surface. Some terahertz sensory systems may include a visual alignment tool that includes a single visible laser beam aligned with the radiation head for aligning the radiation head. For example, referring to FIGS. 1A and 1B, a laser device 100 that emits a visual laser beam 101 is positioned within a radiation head 102 having an emitter 104 and a detector 106. A mirror 108 is positioned with the laser device 100 such that the visual laser beam 101 passes through a hole 110 in the mirror 108 and onto a target surface 112. If the radiation head 102 is normal to the target surface 112, the visual laser beam 101 reflects from the target surface 112 at one reflection point and a reflected laser beam will travel back up through the hole 110 of the mirror 108. If the radiation head 102 is not normal to the target surface 112, the reflected laser beam does not pass through the hole 110 and instead hits the mirror 108 to produce a second reflection point on the target surface 112 (FIG. 1B) that is visible. While the laser beam technique provides a visual tool for aligning the radiation head, the technique may not identify an optimal normal position due to, for example, inaccurate alignment between the visual laser beam and the radiation beam from the radiation head.

The present disclosure is directed toward a method and system for aligning the radiation head with the target surface to identify an optimal normal of the radiation head with respect to the target surface. As described further herein, in one form, a scan of a selected area of the target surface is performed with the radiation beam, and an optimal normal position (i.e., a normal position) of the radiation head is determined based on a peak amplitude of one or more reflected radiation signals received by the radiation head.

Figure 2:
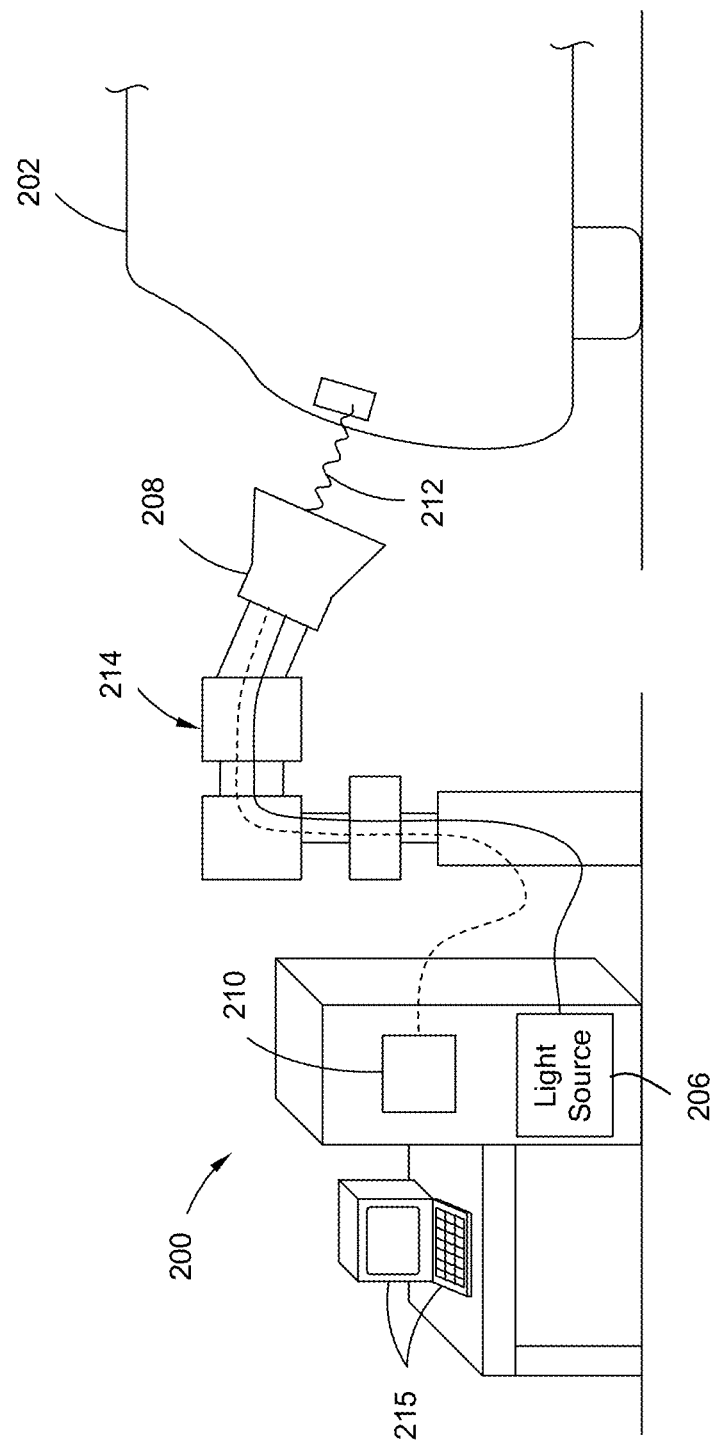
FIG. 2 is a schematic view of a terahertz sensory system in accordance with the teachings of the present disclosure.

Referring to FIG. 2, a terahertz (THz) sensory system 200 for measuring the thickness of a one or more paint layers on a vehicle body 202 is provided. The system 200 includes a THz light source 206, a radiation head 208 coupled to the light source 206, and a controller 210. The light source 206 is operable to generate a radiation beam 212 within the THz frequency range. Accordingly, the radiation beam 212 is in a region of the electromagnetic spectrum that includes microwaves and infrared light waves. The radiation beam 212 can penetrate a wide variety of materials and travel in a line of sight.

Figure 3:
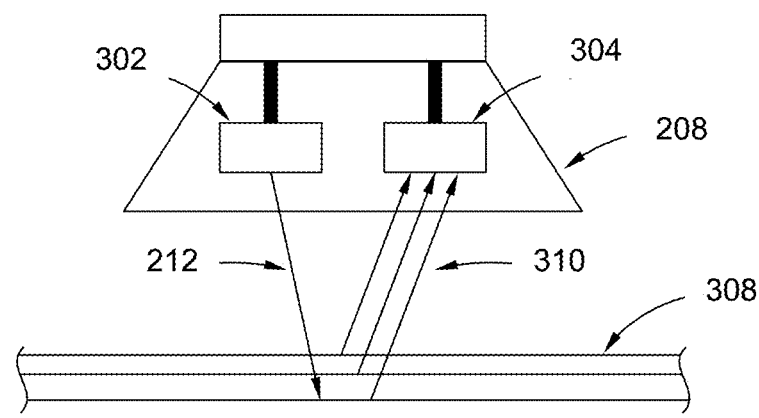
FIG. 3 is a schematic of a radiation head of the terahertz sensory system in accordance with the teachings of the present disclosure.

In one form, the radiation head 208 is coupled to the light source 206 by way of a fiber optic cable, and is arranged and attached to a moveable member 214, such as a robotic arm. The moveable member 214 is operable to adjust the orientation and the position of the radiation head 208. Referring to FIG. 3, the radiation head 208 includes an emitter 302 and a detector 304. The emitter 302 emits or radiates the radiation beam 212 generated by the light source 206 toward a target surface 308 along the vehicle body 202. The detector 304 receives one or more reflected radiation beams 310 reflected from the vehicle body 202. The radiation head 208 is communicably coupled to the controller 210 by way of, for example, wires, and transmits one or more reflected radiation signals indicative of the reflected radiation beams 310 to the controller 210.

The controller 210 is a computer that includes, for example, a processor, a computer readable medium, and other electronic components. The controller 210 is further connected to one or more user interface 215, such as a keyboard and a monitor (e.g., liquid crystal display) for allowing an operator to view one or more graphical user interfaces for operating the system 200.

The controller 210 is configured to perform a paint thickness analysis (i.e., a film build analysis) by operating the light source 206 and the radiation head 208 to emit the THz radiation beam 212 toward the target surface. Based on the reflected radiation signals, the controller 210 is configured to determine the thickness of one or more paint layers of the target surface 308. An example of such analysis is provided in Applicant's co-pending application, U.S. Ser. No. 14/829,888, filed Aug. 19, 2015 and titled "ROBOTIC VEHICLE PAINTING INSTRUMENT INCLUDING A TERAHERTZ RADIATION DEVICE" which is commonly owned with the present application and the contents of which are incorporated herein by reference in its entirety.

Figure 4:
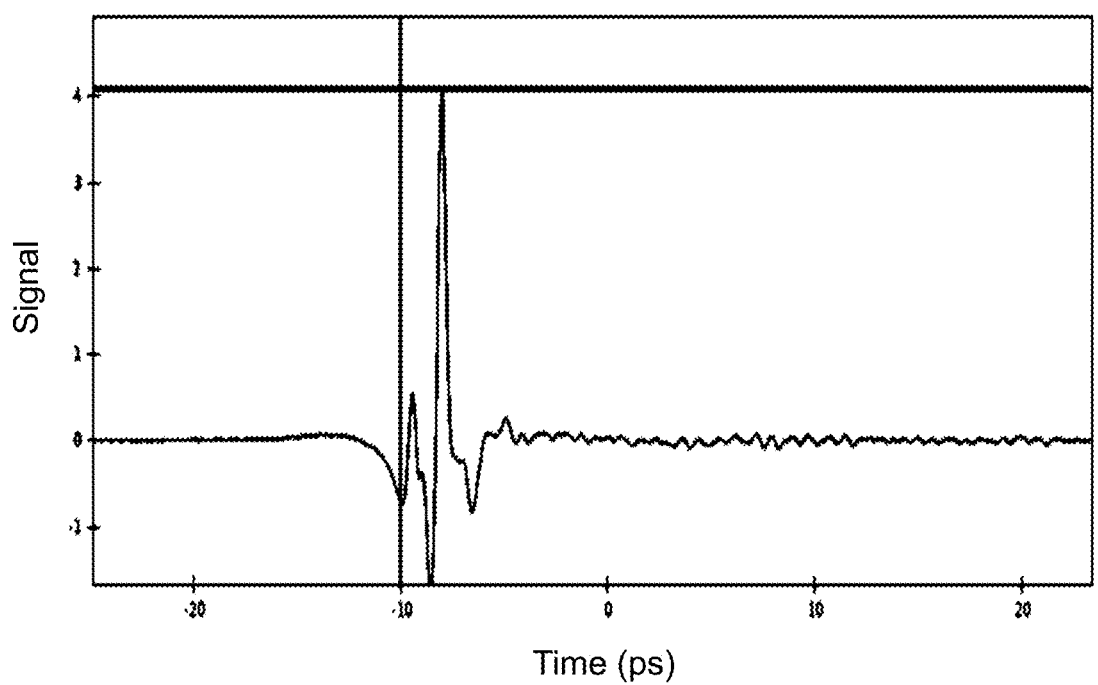
FIG. 4 is a graph illustrating a waveform of a reflected radiation signal in accordance with the teachings of the present disclosure.

Generally, the radiation beam 212 reflects off the paint layers, due to a change in refractive index, and the time difference of the reflection is used to calculate the thickness. In one form, the peaks of the waveform corresponding to the reflected radiation signals coincide with a first beam reflected from a clearcoat surface and a second beam reflected from a substrate. For example, FIG. 4 is a graph of an example waveform of reflected radiation signals. The two peak amplitudes are indicative of reflected beams from two different layers. The waveform may be deconvoluted using a model that is developed from measurements and data obtained from matching single or full film build panels. The model involves cycling through various scenarios of film builds (in a multi-layer system) until the calculated waveform matches the generated waveform. Thus, identifying thickness of the other layers.

Figure 5:
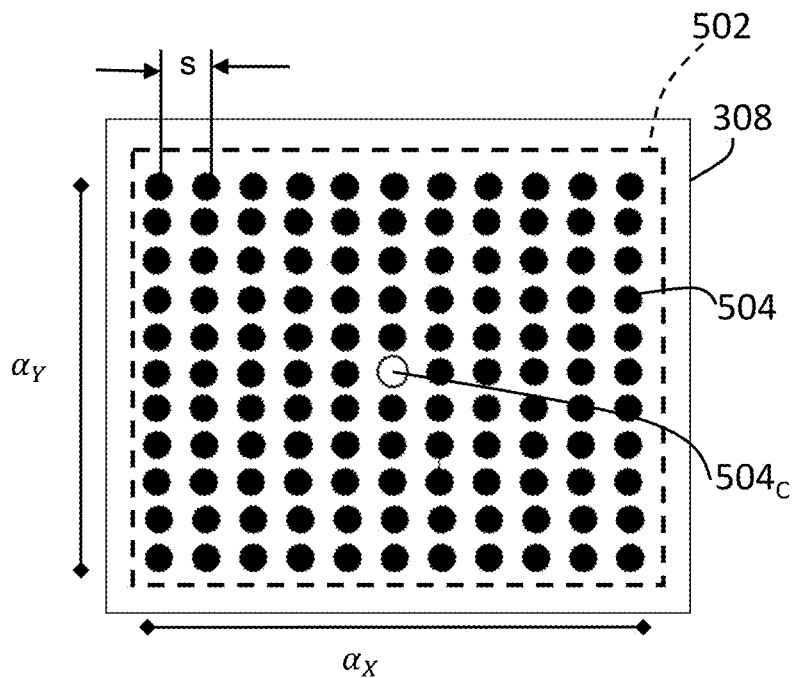
FIG. 5 illustrates a selected area having a plurality of scan points in accordance with the teachings of the present disclosure.

Prior to performing the paint thickness analysis, the controller 212 is configured align the radiation head 208 such that is it normal to the target surface 308. Referring to FIG. 5, in one form, the controller 212 is configured to scan a selected area 502 of the target surface 308 with the radiation beam and identify the normal as a position at which a maximum peak amplitude is detected. In scanning the selected area 502, the controller 212 measures a peak amplitude at a plurality of scan points 504 that are distributed within the selected area 502 at a scan step size (s). More particularly, the controller 212 aligns the radiation head with a subject scan point by operating the moveable member 214, emits the radiation beam 212, and analyzes the reflected radiation signals received to determine the peak amplitude for the subject scan point. Based on the peak amplitudes measured, the scan point associated with the maximum peak amplitude from among the peak amplitudes measures is identified as the normal position along the target surface.

In one form, the selected area 502 is defined by angular ranges along two perpendicular axes (e.g., $\alpha_X$ and $\alpha_Y$) to form a two-dimension region with one of the scan points 504 being a center point $504_C$ of the selected area 502. For example, the angular ranges may be 3 deg for both X and Y axes (e.g., $\alpha_X=\alpha_Y=3$). The angular ranges may be different for the two axes (i.e., $\alpha_X \neq \alpha_Y$) and can be any other suitable range. In one form, the scan step size and/or the angular ranges are adjustable by the operator by way of the user interface 215.

In one form, the plurality of scan points 504 form a square-shaped grid within the selected area 502. Other suitable patterns formed by the scan points 504 are also within the scope of the present disclosure, such as triangle, rectangle, and circle. In addition, the pattern of the plurality of scan points 504 may be set by the operator via the user interface 215 or may be predefined and stored by the controller 210.

In one form, the center scan point $504_C$ represents an estimated normal of the radiation head 208 relative to the target surface 308. The estimated normal is determined using the laser device as described above. Alternatively, the estimated normal is visually determined by the operator without the use of the laser device by aligning the radiation head 208 to the target surface 308 using the moveable member 214 until the radiation head 208 appears to be normal to the target surface 308. In either method, the controller 210 defines the selected area 502 around the estimated normal and scans the area 502 including the estimated normal.

Figure 6:
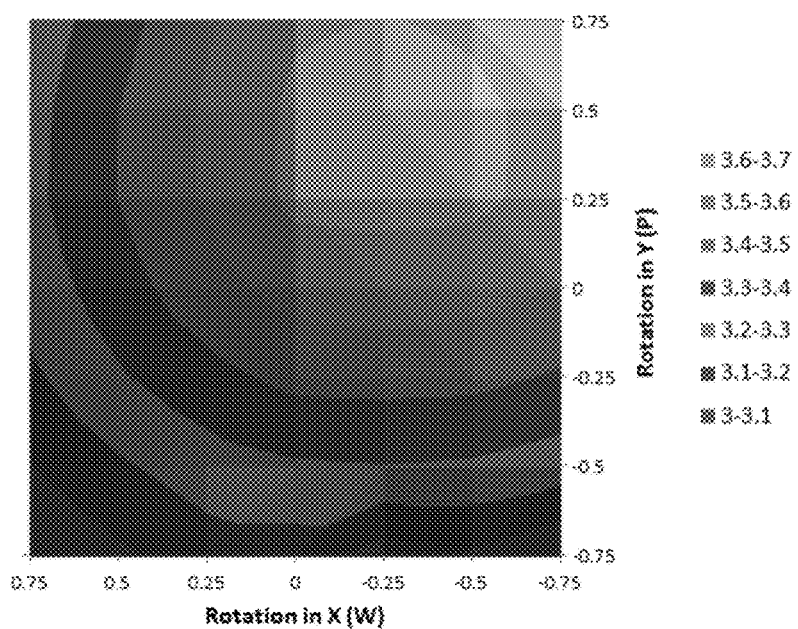
FIG. 6 illustrates a displacement control map in accordance with the teachings of the present disclosure.

Using the peak amplitude, the controller 210 is further configured to generate a displacement control map, which may also be referred to as a contour map, that illustrates the peak amplitudes measured in the selected area 502. For example, FIG. 6 illustrates such a displacement control map for a selected area. In the map, the estimated normal is set at scan point at (0,0); however, the optimal normal, having the maximum peak amplitude between 3.6-3.7, is at a rotation of −0.25° in X-axis (W) and ~0.5° in Y-axis (P). The moveable member 214 could then be offset by those amounts in order to properly orient the radiation head 208.

The displacement control map also illustrates the change in the peak amplitude due to an offset from normal. For example, a rotation of 0.25 in X-axis and 0 in the Y-axis has a peak amplitude of about 3.4 to 3.5, which is about 5% drop from the maximum peak amplitude. Thus, in one form, the data collected during the scanning is used to run a calibration on any point in the grid and determine how being off of normal affects the data collected during the paint thickness analysis. In addition, the allowable variation in angles is also affected by the color of the layer. Accordingly, the data from the paint thickness analysis for a color that is most impacted by changes in small angles is determined and those angle offsets may be used for the system.

Figure 7:
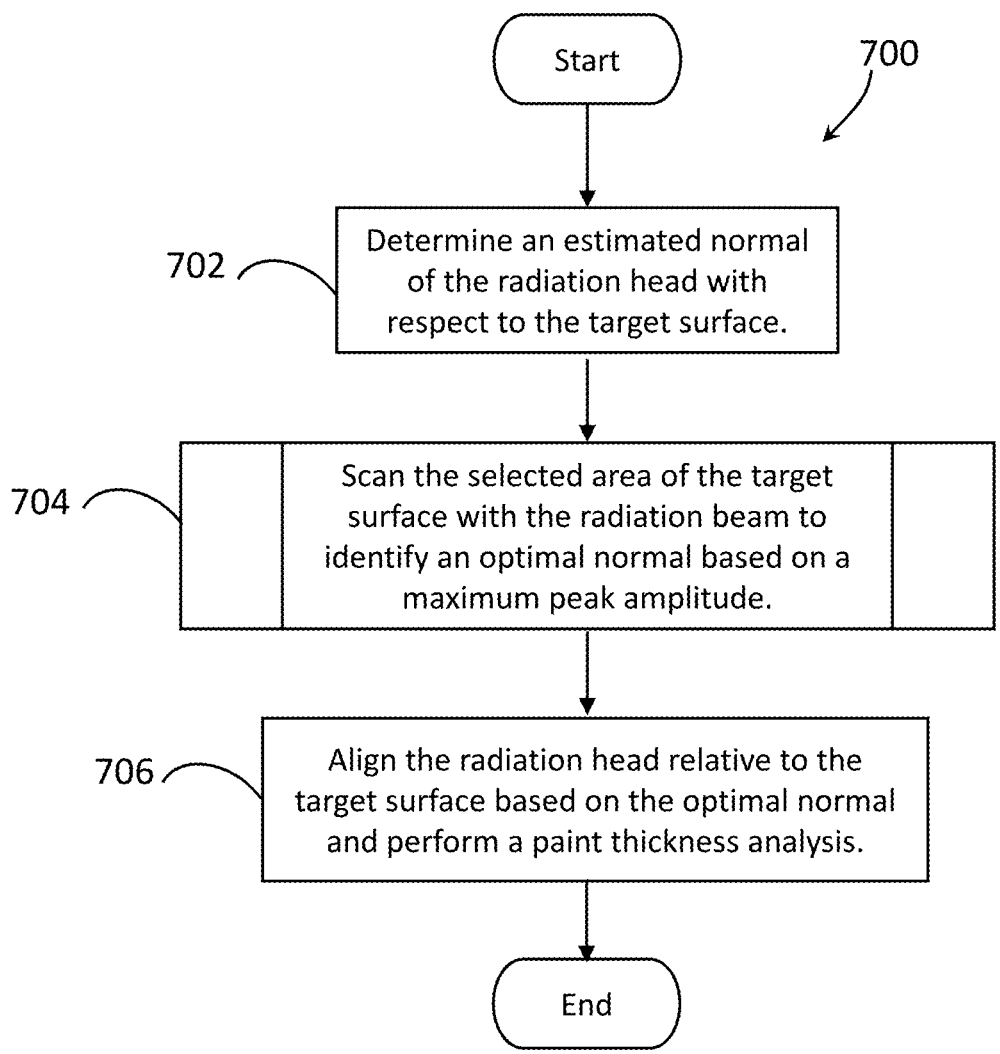
FIG. 7 is a flowchart of a radiation head alignment routine in accordance with the teachings of the present disclosure.
Figure 8:
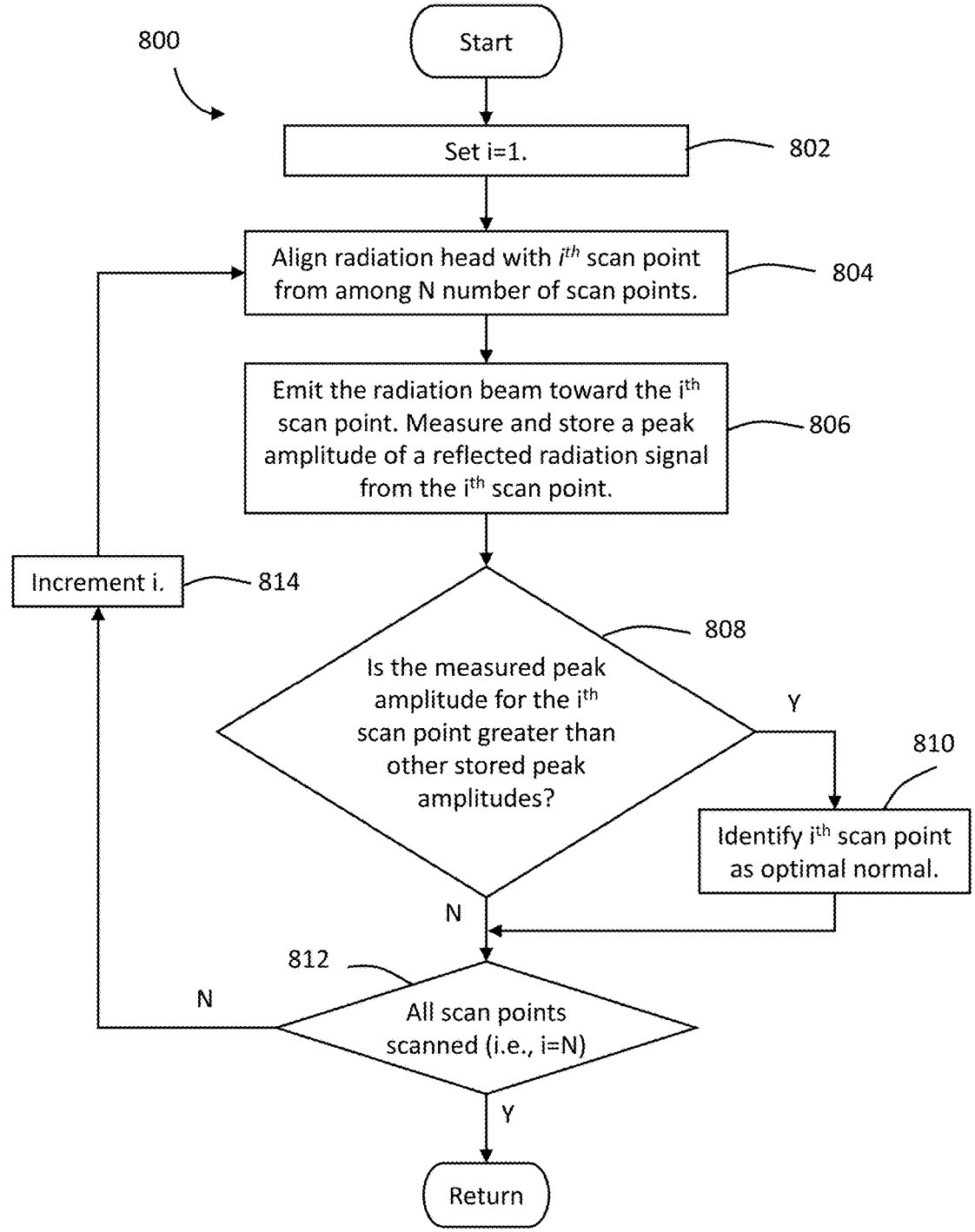
FIG. 8 is a flowchart of a scan routine for the radiation head alignment routine of FIG. 7.

Referring to FIGS. 7 and 8, a radiation head alignment routine 700 performed by the system 200 is provided. At 702, the system determines an estimated normal of the radiation head relative to the target surface. For example, the controller 210 operates a visual alignment tool, such as a laser device equipped with the radiation head 208 to identify an estimated normal. At 704, the system 200 performs a scan of the selected area of the target surface with the radiation beam to identify an optimal normal.

More particularly, in one form, the system 200 executes a scan routine 800 of FIG. 8 from 704 for scanning a selected area having a plurality of scan points, which includes the estimated normal. At 802, the controller 210 sets a counter to 1 (i.e., i=1) to begin scanning at the first scan point. In one form, the positions of the various scan points are determined based on the angle range of the selected area, the scan step size, and the pattern formed by the scan points, which are selectable by the operator. At 804, using the moveable member 214, the controller 210 aligns the radiation head 208 with the $i^{th}$ scan point from among N number of scan points. At 806, the controller 210 operates the radiation head 208 to emit the radiation beam 212 toward the $i^{th}$ scan point, and measures and stores the peak amplitude of a reflected radiation signal.

At 808, the controller 210 determines whether the measured peak amplitude for the $i^{th}$ scan point is greater than other stored peak amplitudes. If so, the controller 210 identifies the $i^{th}$ scan point as being the optimal normal, at 810 and proceeds to 812. If not, the controller 210, at 812, determines whether all of the scan points have been scanned by determining if i is equal to the total number of scan points (i.e., N). If scanning is not complete, the controller 210, at 814, increments the counter and then proceeds to 804 to scan the next scan point. If scanning is complete, the controller 210 returns to 704 of FIG. 7.

From 704, the controller 210 proceeds to 706 to align the radiation head 208 relative to the target surface 308 based on the optimal normal identified by the scan routine 800 using the moveable member 214, and performs the paint thickness analysis.

The routine for aligning the radiation head may be configured in other suitable ways. For example, in one form, the controller 210 scans all of the scan points to measure the peak amplitudes, and then determine the maximum peak amplitude. In addition, the estimated normal may be set by the operator.

The system 200 is configured to identify an optimal normal of the radiation head relative to the target surface by performing a scan of the defined selected area without the use of a new alignment tools. In addition, by identifying the optimal normal based on the strength of the reflected radiation signals, offsets that typically affect such calibration routine are removed from the routine because the system 200 identifies the normal based on signal strength. For example, positional variation of the radiation head caused by the moveable member are not taken into consideration for determining the optimal normal. Instead, the system 200 recognizes that the optimal normal is at a position from which a maximum peak amplitude is received.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for aligning a radiation head of a terahertz sensor system with a target surface, the method comprising:
    scanning a selected area of the target surface with a terahertz radiation beam emitted by the radiation head;
    sensing a peak amplitude for each reflected radiation signal from a plurality of reflected radiation signals received by the radiation head during the scanning of the selected area; and
    identifying a normal position of the radiation head with respect to the target surface based on a maximum peak amplitude from among the peak amplitudes of the reflected radiation signals;
    moving the radiation head to the identified normal position;
    emitting a subsequent terahertz radiation beam while the radiation head is aligned at the identified normal position, the subsequent terahertz radiation beam being incident on the target surface at a location of the target surface that is within the selected area that was previously scanned; and
    determining the thickness of one or more coatings on the target surface based on reflected radiation signals from the subsequent terahertz radiation beam.

2. The method of claim 1 further comprising determining an estimated normal of the radiation head with respect to the target surface, wherein the selected area surrounds the estimated normal.

3. The method of claim 2, wherein the scanning of the selected area further comprises scanning a plurality of points in the selected area with the estimated normal being one of the plurality of points.

4. The method of claim 3, wherein the plurality of points is distributed in the selected area at a selected step size forming a two-dimensional region around the estimated normal.

5. The method of claim 2, wherein the determining the estimated normal further comprises:
    emitting, by a light source, a visible light beam toward the target surface to generate one or more illuminated points on the target surface; and
    identifying a position of the radiation head relative to the target surface as the estimated normal when one illuminated point is visible on the target surface.

6. The method of claim 1 further comprising generating a displacement control map of the selected area, wherein the displacement control map associates the peak amplitudes of the reflected radiations signals with regions of the selected area from which the reflected radiation signal originated from.

7. The method of claim 6, wherein the region associated with the maximum peak amplitude from among the peak amplitudes is indicative of the normal position of the radiation head with the selected area.

8. The method of claim 1, wherein the scanning of the selected area further comprises:

adjusting, by way of a moveable member, an angular position of the radiation head with respect to the target surface to scan a plurality of points that are distributed in the selected area; and at each of the plurality of points, emitting the terahertz radiation beam and receiving at least one of the reflected radiation signals from the plurality of reflected radiation signals.

9. The method of claim 8 further comprising generating a displacement control map that associates the plurality of points with respective peak amplitudes.

10. A terahertz sensor system comprising:
a moveable member;
a terahertz sensor including:
a radiation head attached to the moveable member and is operable to emit a radiation beam and receive one or more reflected radiation beams reflected from a target surface,
  a mirror defining a mirror surface and an aperture open through the mirror, the mirror surface facing toward the target surface,
  an optical laser configured to emit an optical laser beam through the aperture of the mirror onto the target surface, and
  a controller configured to analyze a peak amplitude of a reflected radiation signal that is indicative of the reflected radiation beam, wherein controller is configured to operate the moveable member to scan a selected area of the target surface with the radiation beam, and identify a normal of the radiation head with respect to the target surface based on a maximum peak amplitude from among a plurality of peak amplitudes for a plurality of reflected radiation signals obtained during the scan.

11. The system of claim 10, wherein the controller is configured to identify an estimated normal of the radiation head with respect to the target surface, and define the selected area such that the estimated normal is within the selected area.

12. The system of claim 11, wherein the controller is configured to scan a plurality of points in the selected area with the estimated normal being one of the plurality of points.

13. The system of claim 11 further comprising a visible alignment tool that includes a light source arranged with the radiation head, wherein the controller is configured to operate the light source to emit a visible light toward the target surface, and to identify an estimated normal of the radiation head relative to the target surface when the visible alignment tool generates one visible point along the target surface.

14. The system of claim 10, wherein the controller is configured to adjust an angular position of the radiation head with respect to the target surface by way of the moveable member to scan a plurality of points that are distributed in the selected area, and at each of the plurality of points, the controller operates the radiation head to emit the terahertz radiation beam and receive the reflected radiation beam.

15. The system of claim 10, wherein the controller is configured to operate the moveable member to align the radiation head with the normal after identifying the normal, wherein with the radiation head aligned with the normal, the controller is configured to operate the radiation head to emit a subsequent terahertz radiation beam and to determine the thickness of one or more coatings on the target surface based on reflected radiation signals from the subsequent terahertz radiation beam.

16. The system of claim 10, wherein the moveable member is a robotic arm for adjusting the position of the radiation head.

17. A method for aligning a terahertz radiation head, the method comprising:
  (a) scanning a selected area of the target surface with a terahertz radiation beam via the radiation head;
  (b) sensing a peak amplitude for each of a plurality of reflected radiation signals during the scanning of the selected area;
  (c) identifying a normal of the radiation head relative to the target surface based on a maximum peak amplitude from among the peak amplitudes;
  (d) moving the radiation head to the identified normal position;
  (e) operating the radiation head to emit a subsequent terahertz radiation beam while the radiation head is aligned at the identified normal position, the subsequent terahertz radiation beam being incident on the target surface at a location of the target surface that is within the scanned selected area that was scanned during step (a); and
  (f) determining the thickness of one or more coatings on the target surface based on reflected radiation signals from the subsequent terahertz radiation beam.

18. The method of claim 17, wherein the scanning of the selected area further comprises:
adjusting, by way of a moveable member, an angular position of the radiation head to scan a plurality of points that are distributed in the selected area; and
at each of the plurality of points, emitting the radiation beam and detecting at least one of the reflected radiation signals from the plurality of reflected radiation signals.

19. The method of claim 17 further comprising determining an estimated normal of the radiation head relative to the target surface, wherein the selected area surrounds the estimated normal.

20. The method of claim 19, wherein the scanning the selected area further comprises scanning a plurality of points in the selected area with the estimated normal being one of the plurality of points.

* * * * *